(12) United States Patent
Issinski

(10) Patent No.: US 12,419,604 B2
(45) Date of Patent: Sep. 23, 2025

(54) ENHANCED RESOLUTION STETHOSCOPE

(71) Applicant: Anton Issinski, Coquitlam (CA)

(72) Inventor: Anton Issinski, Coquitlam (CA)

( * ) Notice: Subject to any disclaimer, the term of this patent is extended or adjusted under 35 U.S.C. 154(b) by 320 days.

(21) Appl. No.: 17/956,805

(22) Filed: Sep. 29, 2022

(65) Prior Publication Data

US 2023/0116718 A1    Apr. 13, 2023

Related U.S. Application Data

(60) Provisional application No. 63/254,535, filed on Oct. 12, 2021.

(51) Int. Cl.
*A61B 7/04*    (2006.01)
(52) U.S. Cl.
CPC ........ *A61B 7/04* (2013.01); *A61B 2562/0204* (2013.01)

(58) Field of Classification Search
CPC .... A61B 7/04; A61B 2562/02; A61B 2562/04
USPC .......................................................... 381/67
See application file for complete search history.

(56) References Cited

U.S. PATENT DOCUMENTS

| 2008/0039733 | A1* | 2/2008 | Unver | A61B 7/04 |
| | | | | 600/300 |
| 2008/0154144 | A1* | 6/2008 | Unver | A61B 8/488 |
| | | | | 600/528 |
| 2017/0296138 | A1* | 10/2017 | Shams | A61B 8/565 |
| 2020/0205770 | A1* | 7/2020 | Friedman | H04R 1/46 |

FOREIGN PATENT DOCUMENTS

WO    WO-2019202385 A1 * 10/2019 ........... A61B 5/0006

* cited by examiner

*Primary Examiner* — David L Ton

(57) ABSTRACT

A stethoscope for listening low frequency sounds of a cardiovascular system, that shifts infrasound spectrum produced by moving tissues into a conventional audio spectrum range, making them available for diagnostic purposes. Methods of reading internal infrasounds include ultrasonic tissue position measurements, reconstructing tissue sounds from the Doppler frequency shift, and using electrical cardio potentials as indirect indications of internal sounds.

2 Claims, 4 Drawing Sheets

ENHANCED RESOLUTION STETHOSCOPE

CROSS-REFERENCE TO RELATED APPLICATIONS

This application claims the benefit of the U.S. provisional patent application No. 63/254,535, filed 2021 Oct. 12 by the present inventor.

TECHNICAL FIELD

The present disclosure relates to medical auscultation instruments and more specifically to electric stethoscopes used in auscultation of a cardiovascular system.

BACKGROUND OF THE INVENTION

Auscultation of the cardiovascular system is important, low cost and widely used diagnostic methodology assisting in timely diagnosis of cardiovascular diseases.

One of the most common tools available to physicians to perform auscultation is a stethoscope. Typical stethoscope reads the sound source at the surface of the human body and then outputs it to the stethoscope eartips in a way convenient for the physician to listen.

The main disadvantage of the conventional stethoscope is its limited diagnostic capabilities. Only a set of about ten condition categories are detectable. For wider diagnostic range, alternative methods are required.

Another disadvantage of conventional stethoscopes is a low volume for several classes of sounds. Because human's ear and ability to analyse sounds start decreasing below the frequencies of about 50 Hz, many stethoscopes both mechanical, analog electronic, and digital provide increased amplification of audio signals in this range. Technically it is easily achievable feature of the stethoscope, especially in the electronic or digital models. However, increased sound pressure may cause discomfort or even damage to examiner's ears while still remaining at the subtle recognition levels.

Available Alternatives to the Stethoscope

There are technologies and equipment to read blood flow and heart functions such as ultrasonic systems and systems based on Doppler effect. However, such equipment is relatively expensive, bulky, requires a technician to perform the examination and a specialist to interpret the results.

On practice, stethoscopes are used more often because of their size, availability and quick results.

Also, for the telemedicine purposes, a small low-cost digital stethoscope is more convenient.

LIST OF DRAWING REFERENCE NUMERALS

Figure 1:
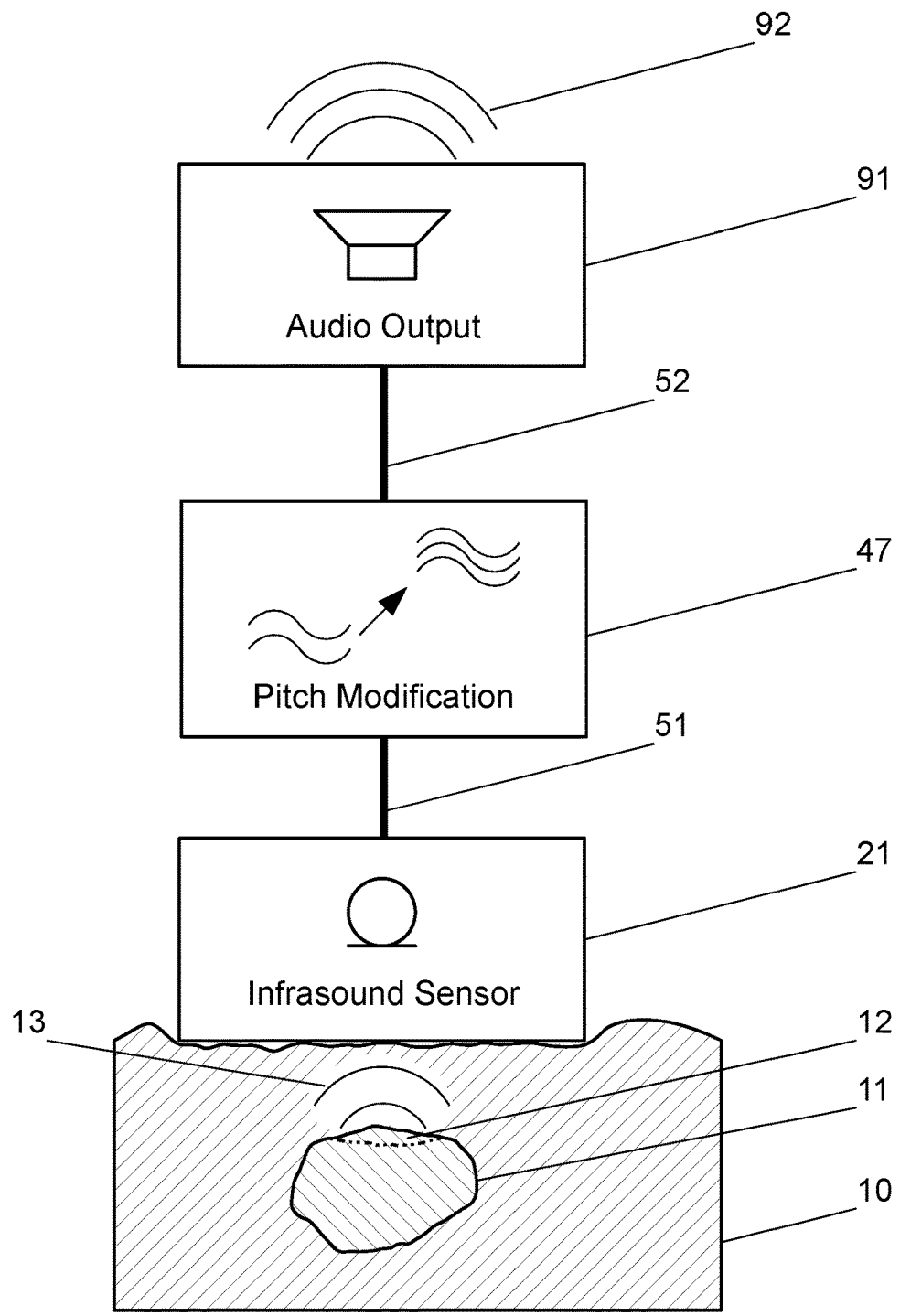
FIG. 1 is a diagram view of a first embodiment that provides access to infrasounds.

10. A living system, or a patient body.
11. A structure or a tissue, such as a heart or a blood vessel under investigation.
12. Tissue movements, or internal sounds, that the stethoscope is reading.
13. Propagation of the internal sounds to the surface of the body, when it is present.
14. Propagation of the emitted ultrasonic wave towards the tissue under investigation.
15. Propagation of the ultrasonic wave that reflected from the tissue under investigation.
18. Electrical potentials or electrical currents produced by cardio or other living structure.
21. An input data acquisition element. The one shown is capable of reading infrasound spectrum.
23. Generic input data acquisition element.
25. Input data acquisition element that utilizes ultrasound technology.
28. Input data acquisition element that measures electric currents or potentials of the body.
31. Ultrasonic wave transmitter.
32. Ultrasonic wave receiver.
35. An electrode that measures electric potential or current.
36. An electrode that measures electric potential or current.
47. Signal processing element. The one that is shown performs pitch modification.
48. Signal processing element. The one that is shown performs time stretching.
51. Information, or an intermediate input signal entering signal processing element.
52. Information, or an intermediate output signal entering audio output element.
91. Audio output element.
92. Audio sounds.

DETAILED DESCRIPTION OF THE INVENTION

Presence of Hidden Infrasounds

It is common understanding in the modern medicine that the human's heart is producing sounds in the range from 10 to 200 Hz. See, for example, publication "Digital stethoscope: technology update" in Medical Devices: Evidence and Research 2018:11 29-36 and the references there. This is likely the reason why modern conventional stethoscopes do not pay attention to the frequencies below 20 Hz.

On the other hand, from the physics point of view, humans' cardiovascular system performs periodic mechanical movements with a period of about 1 second or with the main frequency of about 1 Hertz (Hz), which is also called a patient's pulse rate. This system is inherently complex and non-linear, resulting in numerous harmonics in the frequency domain.

It was recognized in the course of development of the disclosed stethoscope, that the frequency spectrum of the cardiovascular movements, also referenced as sounds in this disclosure, is a function that has a maximum near the main frequency of patient pulse rate of 1 Hz, and then gradually decreases to zero at about 200 Hz.

An indirect indication that this spectrum has a maximum near the pulse rate is an electrocardiogram. In the time domain, it is a relatively smooth curve with the period of 1 second. Because it is mostly smooth, it means that it will be well described by its first say 10 to 20 harmonics. This means that the electrocardiogram has most of its spectrum residing below 20 Hz, while providing vitally important information to the cardiologist.

Hence it is expected for most patients and conditions that a significant amount of information carried by cardiovascular sounds also reside in the lower portion of the spectrum, such as below 20 Hz.

However, the human's ear and associated neuro-intelligence system is capable of hearing and recognizing sounds only above the frequency of 20 Hz.

Hence, the spectrum from 1 Hz to 20 Hz, also called infrasound spectrum, is unaccessible for examination with a conventional stethoscope.

Even above 20 Hz threshold and up to about 50 Hz, the ability of human's brain to recognize and analyse such sounds is lower than for the sounds in the range above 50 Hz. The size of this marginal range also depends on the individual examiner and hence the diagnosis ability will vary with the examiner.

For example, a typical peripheral artery pulsation, despite of its intense amplitude, will result in no sounds if listened with a conventional stethoscope.

Access to Infrasounds

The disclosed stethoscope makes it possible for a physician to listen to the human body sounds in the frequency domain range starting from below human ear ability threshold of 20 Hz and all the way up of the conventional stethoscope frequency of about 200 Hz.

It also makes listening to the sounds in the marginal range of 20 to 50 Hz more reliable and consistent from the examiner to the examiner.

One embodiment of the disclosed stethoscope will read body sounds in the range starting from about 1 Hz and then convert them into the sounds with the frequency domain range above 20 Hz that will be accessible to the human comprehension in the real-time as with the conventional stethoscope.

Hence the disclosed stethoscope will provide the examiner with ability to listen to the peripheral artery pulsations of the example above, including deviations of the pulsations caused by abnormal conditions and turbulent flows, as they reside in about 1 to 10 Hz spectrum range.

With the access to the sounds of the peripheral artery pulsations, the examiner will be able to locate the changes along the artery that may be not available with other devices. For example, when the artery is completely blocked by a blood clot, there will be no blood flow through such artery at any of its points and hence neither Doppler scanner nor CT scan with contrast dyes will be able to locate the blockage. At the same time, the pulsation of the blocked artery will still be present up to the point of the blockage, allowing the examiner to find its location by moving stethoscope input sensor along the artery.

Access to Blocked Sounds

Another advantage of the disclosed stethoscope is an ability to access tissue sounds that do not propagate to the surface of the human body, such as brain blood vessels pulsations behind skull walls, and hence are not accessible to examination with a conventional stethoscope.

In this scenario, the disclosed stethoscope input data acquisition unit is using indirect motion detection modality, such as ultrasound Doppler shift effect to measure tissue dynamics, which is still in the regular cardiovascular pulsation frequency spectrum of 1 to 200 Hz, and then forwards these signals to the examiner in either shifted into the 20 Hz-4 kHz acoustic, or raw unmodified spectrum audio sounds with 1-20 Hz portion removed.

Access to Infra-Infra-Sounds

Infra-Infra-Sound is a new term introduced by this disclosure. It means a sound with the characteristic frequency range, required to describe it, significantly below patient pulse rate of 1 Hz. Such sounds can be viewed as slow changes in the patient's pulse rate, intensity, shape and other properties over time intervals grater than pulse period itself.

It can be listened with the disclosed stethoscope as follows: First, the examiner records patient's heart sounds using stethoscope input sensor in the range of 1-200 Hz. The duration of such record should be much longer than the one pulsation period of 1 second and say is set to 10 minutes. Then the examiner plays back the recorded signals at the speed say 30 times faster. The playback will last 20 seconds and sound as a motor or pump working at the 1800 RPM. However, the sound will be changing with time at a rate anywhere from a fraction of a second to the duration of the entire recording of 20 seconds as in our example.

Such changes in the playback sound in time is by this definition is the Infra-Infra-Sound.

This Infra-Infra-Sound can also be used for diagnostic purposes. It can be combined with various external conditions, such as physical exercise or relaxation period.

Improved Resolution with Time Stretching

The disclosed stethoscope also has an ability to increase time-domain resolution of traditional heart sounds, even in the classical audio 20-200 Hz domain.

A normal human has an ability to distinguish events separated in time only up to some period of about 0.1-0.2 seconds. However, changes in the heart sounds may be faster than such time intervals.

The disclosed stethoscope has an option to reproduce sounds in slow motion mode without changing its pitch, also known as time stretching. This gives the examiner more time to react on the sound change and the ability for more accurate sound location inside the pulse phase.

Structural Description of the Stethoscope

In several embodiments, the disclosed stethoscope will consist of the following components, FIG. 1.

First, there will be an input data acquisition element 21. It will convert processes 12 in the patient tissues 11 into intermediate signals 51.

The input data acquisition element 21 itself normally further consists of the following parts:
- an input sensor or an array of input sensors that read tissue movements 12 and output them in a form of analog electrical signals,
- a part commonly referenced as a signal converter that converts the analog electrical signals into discrete digital signals.

Depending on the sensor type described in more details below, the signal converter can be a simple Analog to Digital Converter (ADC) or more sophisticated device if, for example, an ultrasonic wave time-to-travel or phase shift is measured.

Second, there will be an element 47 that modifies the input digital signals 51 according to a selected function of the stethoscope. Most common name used for this element is a signal processing element or a Digital Signal Processing (DSP) element.

The third component will be an element 91 that converts modified signals obtained from the DSP output 52 into the audio sounds 92 that the examiner will be listening.

Different embodiments of each element described in this disclosure are logically independent on the embodiments of other elements of the stethoscope and hence the entire set of disclosed embodiments should be considered as a combination of all such individual element embodiments.

Handheld and Stationary Models

While the word stethoscope normally refers to a portable device that physician carries with her/him and from one patient to another, the present disclosure is not restricted to only such portable devices.

Because front-end data acquisition units 21, 23, 25, 28 with different modalities may be implemented as different components, because some elements such as signal processing elements 47, 48 may require continues external power supply and for other reasons, the stethoscope definition of the present disclosure also extends to models that may be less portable or more stationary such as ones that are, for example, attached to a wall of the examination room and/or with multiple front-end data acquisition units shared by a single signal processing unit 47, 48.

Even further, because of its potential complexity or other reasons, various parts of the disclosed stethoscope, such as signal processing elements 47 or 48, may be distributed across various places, including locating remotely and operated over communication networks.

Data Acquisition Element

The input front-end of the disclosed stethoscope is a sensor that reads movements of the human body structures such as heart tissues, blood stream or blood vessel walls.

In most cases, this sensor will fall under one of the following categories:

Direct Conversion Sensor

Such sensor will convert the whole or some portion of its position, velocity, acceleration, pressure etc into an analog electrical signal. Most of such sensors will be passive, meaning that they will not actively emit any waves or energy into the patient tissues, but instead will be reading what the tissue provide on its own.

An example of such sensor will be a low-frequency audio microphone, a geophysical exploration geophone, a piezoelectric sensor, a capacitance sensor or a MEMS (MicroElectroMechanical System) acceleration sensor.

Such sensor normally measure the dynamics of the substance or object that comes into the direct contact with the sensor.

Indirect Motion Measurement Sensor

Such sensor will be in general capable of measuring the motion of the structures that are away from the sensor or do not directly interacting with the sensor elements. Most of such sensors will be active, meaning that they will actively emit waves or energy into the patient tissues and then reading the resulting effects such as reflected signals.

Figure 3:
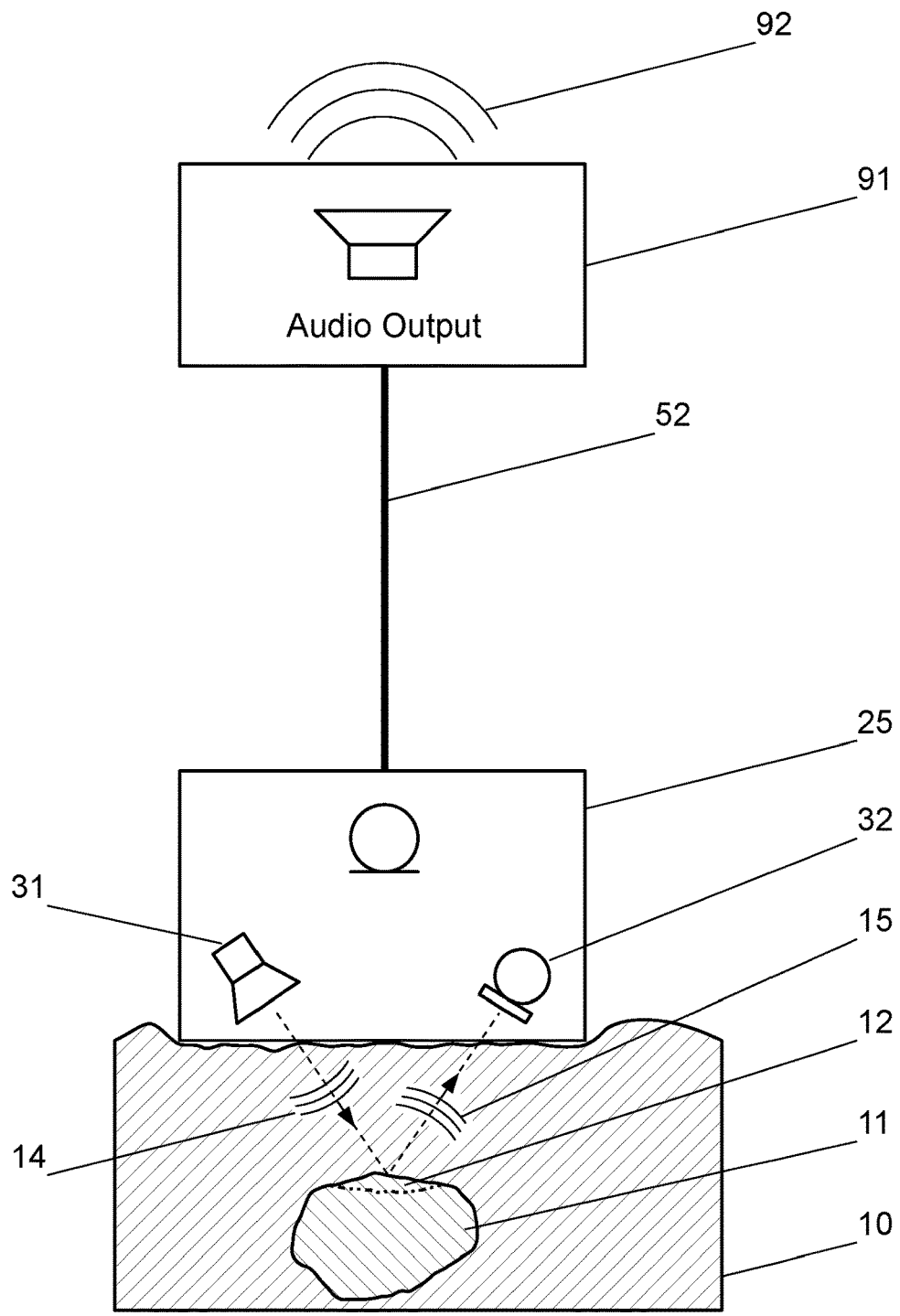
FIG. 3 is a diagram view of a third embodiment that uses an ultrasound indirect motion measurement sensor.

One embodiment is using an ultrasonic wave reflection time to travel information, FIG. 3. In this embodiment, the device shown has a ultrasonic transmitter 31 and an ultrasonic receiver 32. It is possible to combine the transmitter 31 and the receiver 32 into a single element as it is done in most ultrasonic imaging tools. But the simplicity of the disclosed sensor allows to implement them as separate units, which may simplify its construction, use different materials in transmitter and receiver, and position them at desired distances and angles to facilitate selectivity of the sensor.

The sensor's 25 transmitter 31 sending an ultrasonic wave pulse 14 into the patients body 10, receiving the wave pulse reflected 15 from the tissue under the investigation 11, or tissues surrounding it, and then measuring the time it took for the pulse to travel. This time to travel information can be further converted into an instant position of the reflecting surface 12. Continuous measurements of instant position is then used to reconstruct the dynamics, or the sound, of the tissue under investigation 11.

One benefit of such sensor will be an improved access to low frequencies, such as below 4 Hz, comparing to say mechanical direct sound conversion microphone.

Another embodiment example is a Doppler shift ultrasonic sensor. Such sensor will be measuring the frequency or phase shift of the reflected ultrasonic wave. This information can then be used to reconstruct the mechanical movements of the tissues that caused it. The reconstruction process is similar to phase or frequency demodulation used in radio systems: the amplitude of the tissue movement is extracted from the phase shift of the carrier signal, not the amplitude of the carrier signal. The carrier frequency shift is not directly linked with the pitch of the demodulated sound.

The reconstructed tissue dynamics will be a direct representation of the internal body sound and in the original cardiovascular frequency range of about 1 to 200 Hz. It can be further used as the input to the signal processing element (not shown of FIG. 3), or played directly as an audio sound. For example, the similar tissue dynamics would be obtained if an ordinary infrasound microphone was used, if capable of reading the same tissue location.

This is in a contrast to the direct output of an unmodified intermediate signal with the Doppler shift frequency of the reflected ultrasonic wave as a sound. Even if it is in the audio 20 Hz-20 kHz range, it is difficult to use for diagnostics, or even to compare two similar conditions.

The benefit of the indirect motion measurement sensor category is that it can read sounds hidden behind thick or hard surfaces, such as of brain's vessels pulsation behind the skull.

Another benefit is a possibility to select desired areas of the human body, such as a specific chamber, valve, artery, or blood flow, as a source of the sound. This can be done, for example, by using a directional ultrasonic transmitting and receiving elements, or further in the processing software by selecting specific times to travel. The sensor will also reduce the ambient noise and unrelated sounds.

On the other hand, it does not require complexity of the equipment used in ultrasonic imaging, and can be implemented as a small handheld device.

Yet another advantage of this type of sensor comparing to ultrasound imaging is that it emits less ultrasonic energy into the patient's tissues. For imaging, an array of about 200 simultaneously emitting transmitters is required, while the disclosed sensor may work with only one transmitter.

Indirect Factor Sensor

Rather then measuring the tissue movements, such sensor will be measuring other factors that are related, causing or resulted from the tissue movements.

An example would be a passive electric signals measurement sensor, that is using one or several electrodes similar as it is done in the Electrocardiography.

Figure 4:
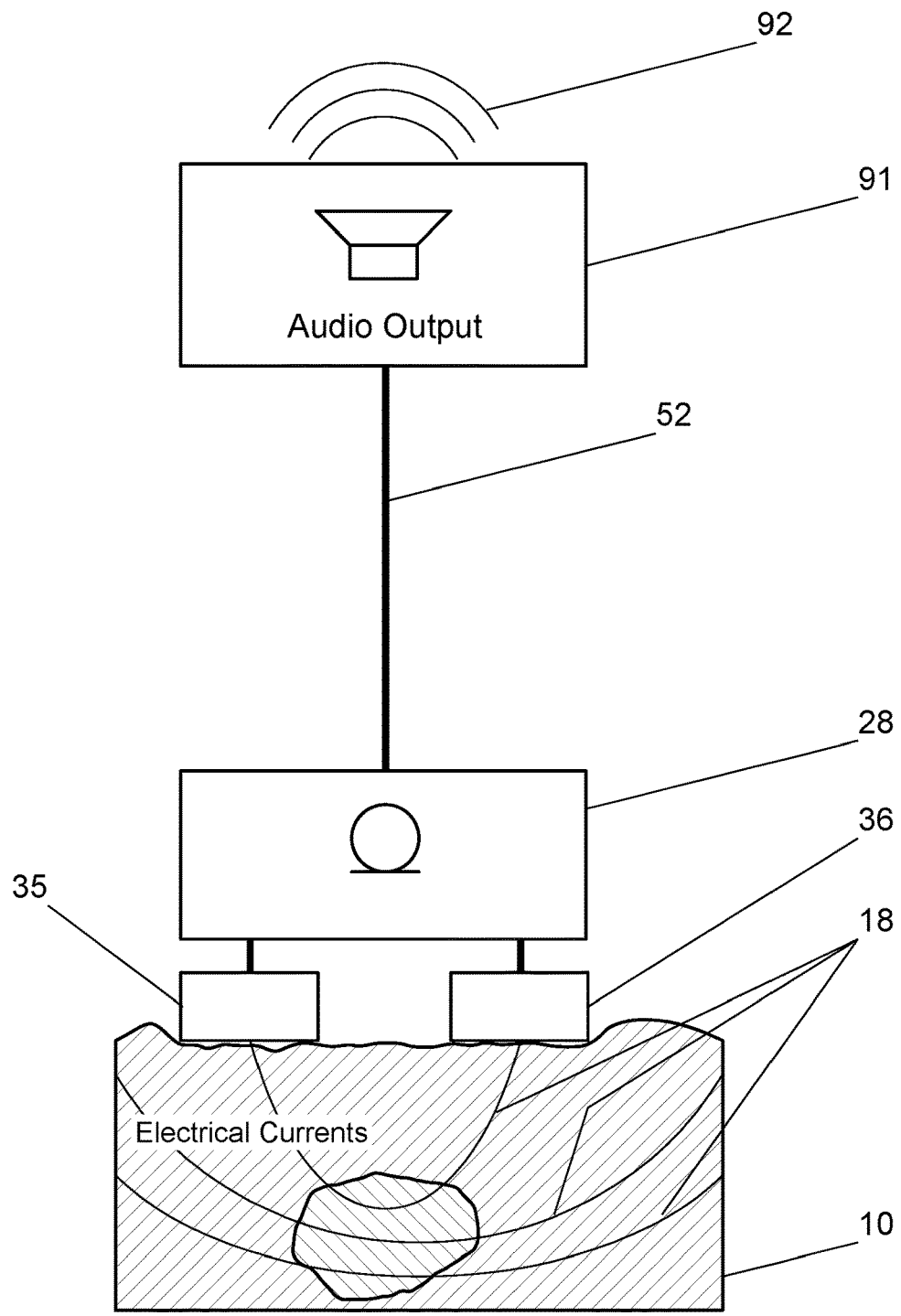
FIG. 4 is a diagram view of a fourth embodiment that uses electrodes to read factors indirectly related to tissue movements.

In this embodiment, FIG. 4, a sensor 28 is not measuring the tissues movements directly. Instead, the sensor 28 has two electrodes 35 and 36 that are attached to the patient's body 10. Electrodes 35, 36 are reading electric potentials, or currents, 18, that are related to the cardiovascular processes. Resulting input signals reside in the 1 to 200 Hz spectrum and hence can be either converted into the audio sounds 92 directly, or modified by the signal processing element (not shown) in a manner described below, for further interpretation by the examiner.

One of the benefits of this sensor is its independence from ambient noise and unrelated sounds.

Signal Processing Element

In the first embodiment, FIG. 1, once the motion information 12 of the body tissue 11 is converted by the input data acquisition element 21 into the input signal 51, it is entered into the second element of the disclosed stethoscope, the signal processing element 47.

The purpose of the signal processing element 47 is to modify the input sound in such a way that it becomes accessible to the humans and suitable for use in medical diagnostic.

On practice, the signal processing functions are often implemented in a digital electronic device, also known as Digital Signal Processing, or DSP, unit. It however can be any other means satisfying criteria described below.

While technically it is possible, and even sometimes more efficient to combine multiple functions such as input data acquisition element 21 and the signal processing element 47 in a single electrical microchip, it is more convenient to view them as separate logical blocks of the disclosed stethoscope, and hence described here as separate elements.

Continuity Criterion of Processing Algorithm

It was recognized in the course of development of the disclosed stethoscope, that to be suitable for medical diagnostic purposes, the entire stethoscope sound transformation process, and in particular the algorithm used in the signal processing element, should satisfy one specific criterion that makes examination results consistent with the input conditions.

The criterion, referred in this disclosure as a continuity criterion, reads as follows:

If two input sounds are similar to each other, then the two corresponding output sounds should also be similar to each other.

In this definition, the word similar means similar as it is perceived by human beings.

If the algorithm does not satisfy this criterion, it will be possible that two identical or very similar patient conditions will result in significantly different output sounds for the examiner, making diagnostic guidelines difficult to define.

One example of two similar sounds would be the same sound with a different volume, or amplitude. Hence to pass said continuity criterion, the signal processing algorithm should not significantly depend on the overall sound volume. If the input sound volume is increased twice, the output sound volume may also increase twice, but we expect that the pitch will remain about the same.

An opposite example of a signal processing algorithm that does not satisfy this criterion would be a DSP unit that performs signal encryption. While the encryption is a one-to-one mapping of input signal onto the output signal that preserves the amount of information presented in the signals, even small changes in the input sound will result in a very different output sound, producing little information to the human being.

Yet another example not satisfying said continuity criterion would be a DSP that performs a frequency modulation, using the input sound as a carrier frequency modulating amplitude. Such modulation is very common and efficient in radio transceivers, but for human beings it removes the natural association between input sound and the output sound: when the amplitude of the input sound increased twice, the pitch of the output sound also increases twice, leading to an impression that it is a different output sound.

Pitch Modification

In the embodiment on FIG. 1, the main function of the signal processing element 47 is to increase the pitch of the sounds produced by the body tissues 13 to the human accessible audio range above 20 Hz, sounds 92.

The signal processing element 47 is taking the input signals 51 that are in the original frequency domain range containing infrasound spectrum, such as 1 Hz-200 Hz, and converting them into the output signals 52 that are in the conventional audio frequency domain, such as 30 Hz to 5 kHz range.

This process when used in the audio systems is commonly known as pitch scaling, pitch shifting or pitch control effects.

In this disclosure pitch modification will be used as a collective term for any of such signal processing action, regardless of its internal implementation and affect on the speed or duration of the sound, as far as it satisfies the continuity criterion described above.

Multiple algorithms of pitch modification are already publicly known at the present time.

Equalizers and other similar frequency band filtering or amplification devices that are used in audio signal processing or conventional electronic stethoscopes, do not perform pitch modifications. For example, such devices will not convert sounds at frequencies below 100 Hz to the sounds that are above 100 Hz, or vise versa.

Time Stretching

Figure 2:
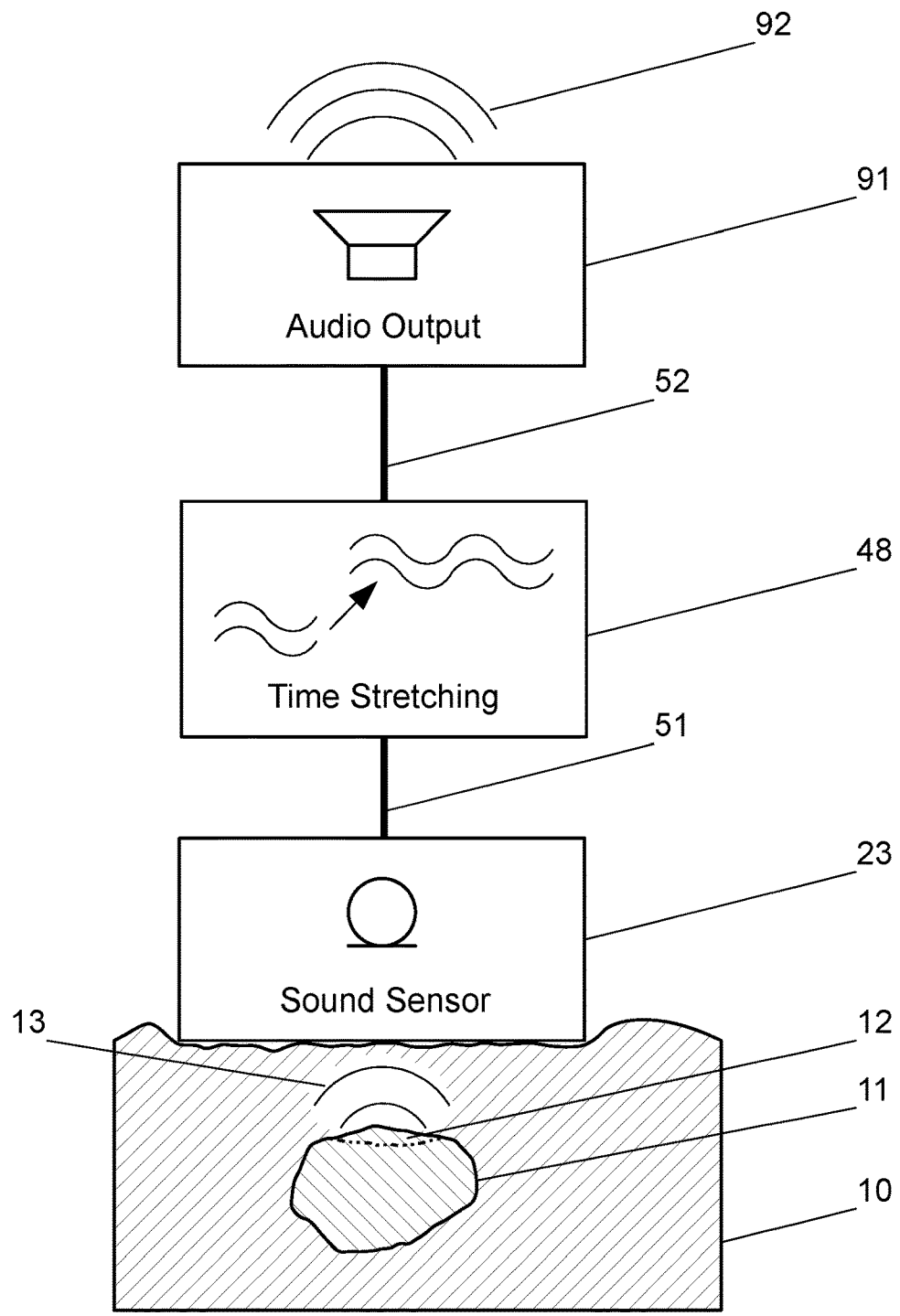
FIG. 2 is a diagram view of a second embodiment that uses time stretching.

In another embodiment, FIG. 2, the main function of the signal processing element 48 is to stretch the sounds in time, without affecting the pitch. In audio industry, this process is known as time stretching.

The time stretching function will allow examiner, for example, to increase heart pulse period from the original 1 second to anywhere from say 2 to 10 seconds.

Such slow motion playback can be used to increase readability or to concentrate on specific areas of the heart or other body tissues sounds.

Similar to pitch scaling, multiple time stretching algorithms are publicly known at the present time.

On the other hand, sometimes instead of stretching, the sound may be required to compress in time, to analyse the slow evolution of sounds in a closer proximity to each other, with or without affecting the pitch. The term time stretching will also apply to such process in this disclosure.

Pitch Increasing Embodiment Example

One specific pitch increasing embodiment example that demonstrates ability of the disclosed stethoscope to listen to a new infrasound spectrum would be as follows.

Lets say the input sensor is reading heart tissue movements in the frequency domain range from 1 to 20 Hz only, which is the infrasound range. To clarify the difference with the conventional stethoscope, sounds above 20 Hz are discarded by the input sensor of this example.

As a first step, multiple heart pulsation periods are recorded into the DSP memory, and then played back at the increased speed, say 30 times faster than originally recorded.

By playing it 30 times faster, the frequency of the output signal will become 30 times higher and reside in the 30 to 600 Hz audio range. If passed to the audio output element 91 directly, for human ear it would resemble a sound of a motor or a pump, working at a main frequency of 30 Hz or 1800 RPM.

As a next step, a second signal conversion stage takes place where the signal processing element is performing a time stretching 30 times. Now the heart pulsation rate is back from 30 Hz to its original rate of about 1 Hz, but the pitch remains as before in the 30 to 600 Hz audio range. The resulting sound can be listened by the examiner.

Information carried by this sound is independent from the information carried by unmodified heart sounds of the audio range accessible by conventional stethoscopes. Hence the disclosed stethoscope provides new capabilities in diagnostic of heart conditions.

If the input sensor would be reading signals in the full 1-200 Hz range, such embodiment stethoscope would produce output spectrum of 30 to 6000 Hz while keeping the puls rate intact.

Effect Amount Parameter

In the above example, a factor of 30 was used to scale the pitch into the higher frequency range.

It is possible that in some cases a less amount of infrasound spectrum is required to analyse, and hence the signal processing element may have a parameter, or an adjustment knob, that will define how much the input sound is modified.

For example, the above factor can be set to any value from 1 to 30, where 1 will mean no any modification at all. By gradually increasing this parameter, the examiner can gradually extend the accessible infrasound range.

Such parameter is also a nice to have function for training purposes.

DEFINITIONS

In many cases and everyday life, the word sound refers to a propagation of periodic perturbations of some media, such as air, liquids or human body. It also often assumes an audio range of frequencies of such perturbations between 20 Hz and 20 kHz. In this disclosure, the word sound means perturbations of media, such as heart tissue or blood vessel walls movements, but not necessarily the effect of propagating them with the time in space. Perturbations with frequencies below 20 Hz will be also considered sounds.

For example, a pulsation of an artery at a main frequency of 1 Hz will be referenced as a sound, despite the fact that the human's ear cannot hear it.

The word audio will be reserved exclusively for sounds that are reliably recognizable by humans, with the frequency range residing approximately from 25 Hz to 20 kHz.

Word infrasound will be used exclusively for sounds with the frequency spectrum residing below of the reliable recognition by humans. If some people still can hear a presence of a sound but others are not because it is too low in pitch, we will use the word infrasound. Infrasound spectrum is starting at approximately 25 to 30 Hz, depending on a type of its use, and goes down to zero.

Similar, an auscultation as a process of listening to the internal sounds of the body, or any living system, extends in this disclosure into the infrasound spectrum.

Word signal, such as in phrases input signal or output signal, will refer to any type of information, either transmitted, relayed, communicated or stored. Most often in modern devices signals are implemented as analog or digital electrical currents, electromagnetic waves, network communication, or storage items.

The word examiner is used to describe a person, often a physician or other health practitioner who evaluates patient conditions.

The invention claimed is:

1. A device for listening to internal sounds of a living system, comprising:
    an input data acquisition element that reads said internal sounds of said living system and converts them into an input signal,
    a signal processing element that takes said input signal and converts it to an output signal,
    an audio output element that takes said output signal and converts it into audio output sounds,
    said signal processing element performing a pitch modification of said input signal in the process of converting it to said output signal,
    whereby infrasound spectrum of said internal sounds can be listened in an audio spectrum range of said audio output sounds and hence used for medical diagnostic purposes.

2. A device for listening to internal sounds of a living system, comprising:
    an input data acquisition element that reads said internal sounds of said living system by means of ultrasound sending and receiving process and converts them into an input signal,
    an audio output element that takes said input signal and converts it into audio output sounds,
    where the process of converting said internal sounds into said audio output sounds satisfies a continuity criterion,
    whereby said internal sounds could be accessed deep inside the body or in a selective manner.

* * * * *